US009926240B2

(12) United States Patent
Ward

(10) Patent No.: US 9,926,240 B2
(45) Date of Patent: Mar. 27, 2018

(54) PROCESS FOR PRODUCING BTX FROM A C5-C12 HYDROCARBON MIXTURE

(71) Applicant: SAUDI BASIC INDUSTRIES CORPORATION, Riyadh (SA)

(72) Inventor: Andrew Mark Ward, Norton (GB)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 2 days.

(21) Appl. No.: 14/403,883

(22) PCT Filed: Jun. 4, 2013

(86) PCT No.: PCT/EP2013/061425
§ 371 (c)(1),
(2) Date: Nov. 25, 2014

(87) PCT Pub. No.: WO2013/182534
PCT Pub. Date: Dec. 12, 2013

(65) Prior Publication Data
US 2015/0166434 A1 Jun. 18, 2015

(30) Foreign Application Priority Data
Jun. 5, 2012 (EP) .................................... 12004292

(51) Int. Cl.
C07C 4/06 (2006.01)
B01J 35/00 (2006.01)
B01J 23/42 (2006.01)
B01J 29/40 (2006.01)
C10G 45/62 (2006.01)
C10G 45/64 (2006.01)
C10G 47/00 (2006.01)
C10G 47/14 (2006.01)
C10G 47/18 (2006.01)
C10G 47/22 (2006.01)
C10G 65/10 (2006.01)
B01J 21/04 (2006.01)
(Continued)

(52) U.S. Cl.
CPC ................ C07C 4/06 (2013.01); B01J 21/04 (2013.01); B01J 21/08 (2013.01); B01J 23/42 (2013.01); B01J 29/40 (2013.01); B01J 35/0006 (2013.01); B01J 35/1019 (2013.01); B01J 35/1042 (2013.01); B01J 35/1061 (2013.01); C07C 4/14 (2013.01); C10G 45/62 (2013.01); C10G 45/64 (2013.01); C10G 45/70 (2013.01); C10G 47/00 (2013.01); C10G 47/14 (2013.01); C10G 47/18 (2013.01); C10G 47/22 (2013.01); C10G 65/10 (2013.01); C07C 2529/44 (2013.01); C10G 2300/1044 (2013.01); C10G 2400/30 (2013.01)

(58) Field of Classification Search
CPC ... B01J 21/04; B01J 21/08; B01J 23/42; B01J 29/40; B01J 35/0006; B01J 35/1019; B01J 35/1042; B01J 35/1061; C07C 2529/44; C07C 4/06; C07C 4/14; C10G 2300/1044; C10G 2400/30; C10G 45/62; C10G 45/64; C10G 45/70; C10G 47/00; C10G 47/14; C10G 47/18; C10G 47/22; C10G 65/10
USPC ....... 585/322, 303, 300, 477, 481, 482, 488, 585/489; 208/65, 66, 138, 51, 85, 135, 208/137, 140
See application file for complete search history.

(56) References Cited

U.S. PATENT DOCUMENTS 3,433,848 A 3/1969 Devins et al.
3,517,078 A 6/1970 Simonetta
(Continued)

FOREIGN PATENT DOCUMENTS

JP S496300 B1 2/1974
WO 0244306 A1 6/2002
(Continued)

OTHER PUBLICATIONS

International Search Report for International Application No. PCT/EP2013/061425; International Filing Date: Jun. 4, 2013; Date of Mailing: Aug. 23, 2013; 5 Pages.
(Continued)

Primary Examiner — Sharon Pregler
(74) Attorney, Agent, or Firm — Cantor Colburn LLP

(57) ABSTRACT

The present invention relates to a process for producing chemical grade BTX from a mixed feedstream comprising C5-C12 hydrocarbons by contacting said feedstream in the presence of hydrogen with a catalyst having hydrocracking/hydrodesulphurization activity. Particularly, a process for producing BTX from a feedstream comprising C5-C12 hydrocarbons is provided comprising the steps of: (a) contacting said feedstream in the presence of hydrogen with a combined hydrocracking/hydrodesulphurization catalyst to produce a hydrocracking product stream comprising BTX; and (b) separating the BTX from the hydrocracking product stream. The hydrocracking/hydrodesulphurization catalyst comprises 0.1-1 wt-% hydrogenation metal in relation to the total catalyst weight. The hydrocracking/hydrodesulphurization catalyst further comprises a zeolite having a pore size of 5-8 Å and a silica ($SiO_2$) to alumina ($Al_2O_3$) molar ratio of 5-200. The hydrocracking/hydrodesulphurization conditions include a temperature of 450-580° C., a pressure of 300-5000 kPa gauge and a Weight Hourly Space Velocity of 0.1-10 $h^{-1}$.

20 Claims, No Drawings

(51) Int. Cl.
  *B01J 21/08* (2006.01)
  *B01J 35/10* (2006.01)
  *C10G 45/70* (2006.01)
  *C07C 4/14* (2006.01)

(56) References Cited

U.S. PATENT DOCUMENTS

| | | | |
|---|---|---|---|
| 3,957,621 A | 5/1976 | Bonacci et al. | |
| 5,792,338 A * | 8/1998 | Gosling | C10G 35/095 208/64 |
| 6,001,241 A * | 12/1999 | Gosling | C10G 35/095 208/138 |
| 7,297,831 B2 * | 11/2007 | Lee | C10G 35/085 585/489 |
| 7,563,358 B2 * | 7/2009 | Stavens | B01J 29/126 585/489 |
| 8,168,844 B2 * | 5/2012 | Arca | C10G 47/18 585/489 |
| 2006/0287561 A1 | 12/2006 | Choi et al. | |
| 2007/0112237 A1 | 5/2007 | Lee et al. | |
| 2008/0051615 A1 | 2/2008 | Stavens et al. | |
| 2009/0272672 A1 | 11/2009 | Arca et al. | |

FOREIGN PATENT DOCUMENTS

| | | |
|---|---|---|
| WO | 2007055488 A1 | 5/2007 |
| WO | 2008015027 A1 | 2/2008 |
| WO | 2010102712 A2 | 9/2010 |

OTHER PUBLICATIONS

Karge et al., "Molecular Sieves: Science and Technology," vol. 3, (2002) pp. 204-255.

Kirk-Othmer Encyclopedia of Chemical Technology, "Molecular Sieves," Fifth Edition, vol. 16, (2006), pp. 811-852.

Le Page, "Applied Heterogeneous Catalysis: Design, Manufacture, Use of Solid Catalysts," (1987) Institut Francais due Petrole Publications; pp. 1-7.

Meyers "Handbook of Petroleum Refining Processes," (1986) McGraw-Hill: Chemical Process Technology Handbook Series; pp. 1-9.

Rase, Handbook of Commercial Catalysts: Heterogeneous Catalysts ed. (2000) CRCPRess p. 211-212.

Scherzer, et al.; "Hydrocracking Science and Technology," (1996) pp. 1-3 (German Language Attached).

Written Opinion of the International Searching Authority for International Application No. PCT/EP2013/061425; International Filing Date: Jun. 4, 2013; Date of Mailing: Aug. 23, 2013; 6 Pages.

Etsuro Nakamura et al., "Studies of C6 to C10 Alkylbenzenes in Crude Oils, Naphthas, Reformates and Cracked Gasolines"; Oil Journal, 1966, vol. 9, No. 8, pp. 634-642 (42-50).

Yamazaki., "Determination of Aromatic Hydrocarbons in Petroleum Preparation by HPLC," Central Customs Laboratory, Ministry of France, 2000, No. 39, pp. 67-69.

Bhirud V. et al. "MaxEne Process-Based Low Capital Petrochemical Complex"; DGMK-Conference "Chances for Innovative Processes at the Interface between Refining and Petrochemistry"; Berlin, 2002, pp. 115-122.

Kirk-Othmer Encyclopedia of Chemical Technology "BTX Processing" in ECT 3rd ed., vol. 4, pp. 264-277, by D. L. Ransley, Chevron, Research Company; in ECT 4th ed., vol. 4, pp. 590-605, by W. A. Sweeney and P. F. Bryan, Chevron Research and Technology Company—Publication Dates: Dec. 14, 2007 and Sep. 8, 2010; 17 pages.

Kirk-Othmer Encyclopedia of Chemical Technology; "Benzene"; vol. 3, 2004, pp. 596-624.

Kirk-Othmer Encyclopedia of Chemical Technology, "Fuels, Synthetic Liquid" in ECT 1st ed., vol. 6, pp. 960-983, by J. H. Arnold et al., Hydrocarbon Research, Inc.; Sep. 8, 2010; Carbon Monoxide—Hydrogen Reactions in ECT 2nd ed., vol. 4, pp. 446-489, by H. Pichler et al.; Dec. 4, 2000; ECT 3rd ed., vol. 11, pp. 447-489, by C. D. Kalfadelis and H. Shaw, Exxon Research and Engineering Co., Sep. 8, 2010; 42 Pages.

Kirk-Othmer Encyclopedia of Chemical Technology; "Petroleum Refinery Processes"; vol. 18, 2006, 49 Pages.

* cited by examiner

US 9,926,240 B2

PROCESS FOR PRODUCING BTX FROM A C5-C12 HYDROCARBON MIXTURE

CROSS REFERENCE TO RELATED APPLICATIONS

This application is a 371 of International Application No. PCT/EP2013/061425, filed Jun. 4, 2013, which claims priority to European Application No. 12004292.4, filed Jun. 5, 2012, both of which are hereby incorporated by reference in its entirety.

The present invention relates to a process for producing chemical grade BTX from a mixed feedstream comprising C5-C12 hydrocarbons by contacting said feedstream in the presence of hydrogen with a catalyst having hydrocracking/hydrodesulphurisation activity.

It has been previously described in WO 02/44306 A1 and WO 2007/055488 A1 that aromatic hydrocarbon compounds and LPG can be produced from a mixed hydrocarbon feedstock having boiling points of 30-250° C. Therefore a hydrocarbon feedstock having boiling points of 30-250° C. and hydrogen is introduced to a reaction zone wherein said hydrocarbon feedstock is converted in the presence of a catalyst to aromatic hydrocarbon compounds abundant in BTX through hydrodealkylation and/or transalkylation and to non-aromatic hydrocarbon compounds which are abundant in LPG through hydrocracking and recovering the aromatic hydrocarbon compounds and LPG, respectively, through gas-liquid separation and distillation. The catalyst used in the process of WO 02/44306 A1 comprises platinum/tin or platinum/lead and a mixture support consisting of 10-95 wt % of zeolite having a molar ratio of silica/alumina of 200 or less and 5-90 wt % of inorganic binder, said zeolite being selected from the group consisting of mordenite, beta type zeolite, ZSM-5 type zeolite and a mixture thereof, in which said platinum is present at an amount of 0.01-0.5 parts by weight, and said tin is present at an amount of 0.01-5.0 parts by weight or said lead is present at an amount of 0.02-5.0 parts, on the basis of 100 parts by weight of said mixture support. The catalyst used in the process of WO 2007/055488 A1 is prepared by supporting 0.01~0.5 parts by weight of platinum (Pt) and 0.01~3.0 parts by weight of bismuth (Bi) onto 100 parts by weight of a mixture support, the mixture support including 10~95 wt % of zeolite having a molar ratio of silica/alumina of 200 or less, selected from the group consisting of mordenite, beta zeolite, ZSM-5 zeolite and combinations thereof, and 5~90 wt % of an inorganic binder. The methods of WO 02/44306 A1 and WO 2007/055488 are characterized in that the hydrogenation activity of the hydrogenation metal platinum that is comprised in the catalyst must be inhibited by a secondary metal such as tin, lead or bismuth. As a result thereof, the catalyst becomes highly susceptible to deactivation by contaminants and heteroatoms that are often comprised in hydrocarbon feedstocks such as sulphur. Furthermore, the methods of WO 02/44306 A1 and WO 2007/055488 produce a product stream comprising a relatively high amount of non-aromatic hydrocarbons that co-boil with BTX rendering it impossible to produce chemical grade BTX without using solvent extraction methods and a relatively high amount of fuel gas at the expense of the LPG produced.

It was an object of the present invention to provide a process for converting mixed C5-C12 hydrocarbon feedstream that is relatively rich in BTX and co-boilers of BTX, such as first stage hydro-treated pyrolysis gasoline or straight run naphtha, into chemical grade BTX without the need of solvent extraction to separate the BTX from the co-boiling non-BTX hydrocarbon species. It was furthermore an object of the present invention to provide a process for converting mixed C5-C12 hydrocarbon feedstream to BTX and LPG that is not susceptible to catalyst deactivation caused by the sulphur-comprising compounds in the feed and that does not require desulphurisation of the feedstock prior to feeding to said process. It was furthermore an object of the present invention to provide a process for converting mixed C5-C12 hydrocarbon feedstream to BTX and LPG wherein production of methane is reduced when compared to conventional methods. It was furthermore an object of the present invention to provide a process for converting mixed C5-C12 hydrocarbon feedstream to BTX and LPG wherein conversion of the benzene comprised in the feedstream to other hydrocarbon compounds such as naphthene compounds, toluene or xylene is reduced when compared to conventional methods.

The solution to the above problem is achieved by providing the embodiments as described herein below and as characterized in the claims. Accordingly, the present invention provides a process for producing BTX comprising:

(a) contacting a feedstream comprising C5-C12 hydrocarbons in the presence of hydrogen with a combined hydrocracking/hydrodesulphurisation catalyst comprising 0.1-1 wt-% hydrogenation metal in relation to the total catalyst weight and a zeolite having a pore size of 5-8 Å and a silica ($SiO_2$) to alumina ($Al_2O_3$) molar ratio of 5-200 under process conditions comprising a temperature of 450-580° C., a pressure of 300-5000 kPa gauge and a Weight Hourly Space Velocity of 0.1-10 $h^{-1}$ to produce a hydrocracking product stream comprising BTX; and (b) separating the BTX from the hydrocracking product stream.

In the context of the present invention, it was surprisingly found that by the method of the present invention, a C5-C12 hydrocarbon mixture can be efficiently converted into a mixture comprising substantially no co-boilers of BTX. As a result thereof, chemical grade is obtained by subjecting the hydrocracking product stream by relatively simple separation methods such as gas-liquid separation or distillation. Furthermore, it was found that the amount of methane produced in a process for producing BTX from a feedstream comprising C5-C12 hydrocarbons can be dramatically reduced by the method of the present invention. Methane is an undesired side-product as it has only fuel gas value which is lower than the value of BTX and LPG. A further advantage of the present invention is that the consumption of hydrogen is reduced.

In this context, it is noted that the catalyst used in the processes described in WO 02/44306 A1 and WO 2007/055488 A1 do not utilize a hydrocracking/hydrodesulphurisation catalyst since the presence of the hydrogenation inhibiting secondary metals tin, lead or bismuth render these catalysts unsuitable for hydrodesulphurisation.

As used herein, the term "C# hydrocarbons", wherein "#" is a positive integer, is meant to describe all hydrocarbons having # carbon atoms. Moreover, the term "C#+ hydrocarbons" is meant to describe all hydrocarbon molecules having # or more carbon atoms. Accordingly, the term "C5+ hydrocarbons" is meant to describe a mixture of hydrocarbons having 5 or more carbon atoms.

The product produced by the hydrocracking/hydrodesulphurisation step of the process of the present invention (hydrocracking product stream) comprises LPG, BTX and methane. The term "LPG" as used herein refers to the well-established acronym for the term "liquefied petroleum gas". LPG generally consists of a blend of C2-C4 hydrocarbons i.e. a mixture of C2, C3, and C4 hydrocarbons, wherein C3 hydrocarbons are the main constituents. The term "BTX" as used herein is well known in the art and relates to a mixture of benzene, toluene and xylenes. As used herein, the term "chemical grade BTX" relates to a hydrocarbon mixture comprising less than 5 wt-% hydrocarbons other than benzene, toluene and xylenes, preferably less than 4 wt-% hydrocarbons other than benzene, toluene and xylenes, more preferably less than 3 wt-% hydrocarbons other than benzene, toluene and xylenes, and most preferably less than 2.5 wt-% hydrocarbons other than benzene, toluene and xylenes. Furthermore, the "chemical grade BTX" produced by the process of the present invention comprises less than 1 wt-% 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons. The most critical contaminants are the non-aromatic species which have boiling points close to benzene including, but not limited to, cyclohexane, methylcyclopentane, n-hexane, 2-methylpentane and 3-methylpentane.

Accordingly, the hydrocracking product stream is substantially free from non-aromatic C6+ hydrocarbons. As meant herein, the term "hydrocracking product stream substantially free from non-aromatic C6+ hydrocarbons" means that said hydrocracking product stream comprises less than 1 wt-% non-aromatic C6+ hydrocarbons, preferably less than 0.7 wt-% non-aromatic C6+ hydrocarbons, more preferably less than 0.6 wt-% non-aromatic C6+ hydrocarbons and most preferably less than 0.5 wt-% non-aromatic C6+ hydrocarbons.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

The hydrocracking product stream produced in the process of the present invention preferably comprises less than 5 wt-% of methane. Preferably, the hydrocracking product stream produced in the process of the present invention comprises less than 4 wt-% of methane, more preferably less than 3 wt-% methane, even more preferably less than 2 wt-% methane, particularly preferably less than 1.5 wt-% methane and most preferably less than 1 wt-% methane.

In one embodiment, the hydrocracking product stream produced in the process of the present invention comprises less than 10 wt-% of ethane, preferably less than 8 wt-% ethane, most preferably less than 7 wt-% ethane.

In a further embodiment, the hydrocracking product stream produced in the process of the present invention comprises less than 10 wt-% of methane and ethane, preferably less than 8 wt-% methane and ethane, most preferably less than 7.5 wt-% methane and ethane.

Preferably, the hydrocracking product stream is also substantially free from C5 hydrocarbons. As meant herein, the term "hydrocracking product stream substantially free from C5 hydrocarbons" means that said hydrocracking product stream comprises less than 1 wt-% C5 hydrocarbons, preferably less than 0.7 wt-% C5 hydrocarbons, more preferably less than 0.6 wt-% C5 hydrocarbons and most preferably less than 0.5 wt-% C5 hydrocarbons.

It is a particular advantage of the method of the present invention that the hydrocracking product stream is substantially free from non-aromatic C6+ hydrocarbons as these hydrocarbons usually have boiling points close to the boiling point of C6+ aromatic hydrocarbons. Hence, it can be difficult to separate the non-aromatic C6+ hydrocarbons from the aromatic C6+ hydrocarbons comprised in the hydrocracking product stream by distillation.

The advantageous effects of the process of the present invention are obtained by strategically selecting the hydrocracking/hydrodesulphurisation catalyst in combination with the hydrocracking/hydrodesulphurisation conditions. In the context of the present invention, it was surprisingly found that by combining a hydrocracking/hydrodesulphurisation catalyst having a relatively strong acid function (e.g. by selecting a catalyst comprising a zeolite having a pore size of 5-8 Å and a silica ($SiO_2$) to alumina ($Al_2O_3$) molar ratio of 5-200) and a relatively strong hydrogenation activity (e.g. by selecting a catalyst comprising 0.1-1 wt-% hydrogenation metal) with process conditions comprising a relatively high process temperature (e.g. by selecting a temperature of 450-580° C.), chemical grade BTX and LPG can be produced from a mixed C5-C12 hydrocarbon feedstream without the need of prior desulphurisation of the feedstock, wherein production of methane is reduced and wherein conversion of the benzene comprised in the feedstream to other hydrocarbon compounds such as naphthene compounds, toluene or xylene is reduced.

Accordingly, the hydrocracking/hydrodesulphurisation catalyst comprises a zeolite having a pore size of 5-8 Å, a silica ($SiO_2$) to alumina ($Al_2O_3$) molar ratio of 5-200 and 0.1-1 wt-% hydrogenation metal (in relation to the total catalyst) and the hydrocracking/hydrodesulphurisation conditions include a temperature of 450-580° C., a pressure of 300-5000 kPa gauge and a Weight Hourly Space Velocity of 0.1-10 $h^{-1}$.

The process conditions under which the hydrocracking/hydrodesulphurisation of the feedstream is performed are an important determinant for the composition of the hydrocracking product stream. Preferably, the hydrocracking/hydrodesulphurisation conditions include a temperature of 450-580° C., more preferably of 470-550° C. Lower temperatures must be avoided since hydrogenation of the aromatic ring becomes favorable. This is in stark contrast to the teachings of the prior art in which a relatively low process temperature of up to 430° C. is preferred. In case the reaction temperature is too high, the yield of LPG's (especially propane and butanes) declines and the yield of methane rises. As the catalyst activity may decline over the lifetime of the catalyst, it is advantageous to increase the reactor temperature gradually over the life time of the catalyst to maintain the hydrocracking conversion rate. This means that the optimum temperature at the start of an operating cycle preferably is at the lower end of the hydrocracking temperature range but the optimum reactor temperature will rise as the catalyst deactivates so that at the end of a cycle (shortly before the catalyst is replaced or regenerated) preferably is selected at the higher end of the hydrocracking temperature range.

Preferably, the hydrocracking/hydrodesulphurisation of the feedstream is performed at a pressure of 300-5000 kPa gauge, more preferably at a pressure of 600-3000 kPa gauge, particularly preferably at a pressure of 1000-2000 kPa gauge and most preferably at a pressure of 1200-1600 kPa gauge. By increasing reactor pressure, conversion of C5+ non-aromatics can be increased, but also increases the yield of methane and the hydrogenation of aromatic rings to cyclohexane species which can be cracked to LPG species. This results in a reduction in aromatic yield as the pressure is increased and, as some cyclohexane and its isomer methyl-cyclopentane, are not fully hydrocracked, there is an optimum in the purity of the resultant benzene at a pressure of 1200-1600 kPa.

Preferably, the hydrocracking/hydrodesulphurisation of the feedstream is performed at a Weight Hourly Space Velocity (WHSV) of 0.1-10 $h^{-1}$, more preferably at a Weight Hourly Space Velocity of 0.2-6 $h^{-1}$ and most preferably at a Weight Hourly Space Velocity of 0.4-2 $h^{-1}$. When the space velocity is too high, not all BTX co-boiling paraffin components are hydrocracked, so it will not be possible to achieve BTX specification by simple distillation of the reactor product. At too low space velocity the yield of methane rises at the expense of propane and butane. By selecting the optimal Weight Hourly Space Velocity, it was surprisingly found that sufficiently complete reaction of the benzene co-boilers is achieved to produce on spec BTX without the need for a liquid recycle.

Accordingly, preferred hydrocracking/hydrodesulphurisation conditions thus include a temperature of 450-580° C., a pressure of 300-5000 kPa gauge and a Weight Hourly Space Velocity of 0.1-10 $h^{-1}$. More preferred hydrocracking/hydrodesulphurisation conditions include a temperature of 470-550° C., a pressure of 600-3000 kPa gauge and a Weight Hourly Space Velocity of 0.2-6 $h^{-1}$. Particularly preferred hydrocracking/hydrodesulphurisation conditions include a temperature of 470-550° C., a pressure of 1000-2000 kPa gauge and a Weight Hourly Space Velocity of 0.4-2 $h^{-1}$.

Catalysts having hydrocracking/hydrodesulphurisation activity ("hydrocracking/hydrodesulphurisation catalyst") are described on pages 13-14 and 174 of Hydrocracking Science and Technology (1996) Ed. Julius Scherzer, A. J. Gruia, Pub. Taylor and Francis. Hydrocracking and hydrodesulphurisation reactions proceed through a bifunctional mechanism which requires a relatively strong acid function, which provides for the cracking and isomerization and which provides breaking of the sulphur-carbon bonds comprised in the organic sulfur compounds comprised in the feed, and a metal function, which provides for the olefin hydrogenation and the formation of hydrogen sulfide. Many catalysts used for the hydrocracking/hydrodesulphurisation process are formed by composting various transition metals with the solid support such as alumina, silica, alumina-silica, magnesia and zeolites.

Hydrocracking/hydrodesulphurisation catalysts that are particularly suitable for the process of the present invention comprise a molecular sieve, preferably a zeolite, having a pore size of 5-8 Å.

Zeolites are well-known molecular sieves having a well-defined pore size. As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001). Preferably, the hydrocracking/hydrodesulphurisation catalyst comprises a medium pore size aluminosilicate zeolite or a large pore size aluminosilicate zeolite. Suitable zeolites include, but are not limited to, ZSM-5, MCM-22, ZSM-11, beta zeolite, EU-1 zeolite, zeolite Y, faujastite and mordenite. The term "medium pore zeolite" is commonly used in the field of zeolite catalysts. Accordingly, a medium pore size zeolite is a zeolite having a pore size of about 5-6 Å. Suitable medium pore size zeolites are 10-ring zeolites, i.e. the pore is formed by a ring consisting of 10 $SiO_4$ tetrahedra. Suitable large pore size zeolites have a pore size of about 6-8 Å and are of the 12-ring structure type. Zeolites of the 8-ring structure type are called small pore size zeolites. In the above cited Atlas of Zeolite Framework Types various zeolites are listed based on ring structure. Most preferably the zeolite is ZSM-5 zeolite, which is a well-known zeolite having MFI structure.

The zeolite preferably is dealuminated. Preferably, the silica ($SiO_2$) to alumina ($Al_2O_3$) molar ratio of the ZSM-5 zeolite is in the range of 5-200, more preferably in the range of 10-100. Means and methods to obtain dealuminated zeolite are well known in the art and include, but are not limited to the acid leaching technique; see e.g. Post-synthesis Modification I; Molecular Sieves, Volume 3; Eds. H. G. Karge, J. Weitkamp; Year (2002); Pages 204-255. In the context of the present invention it was found that using a dealuminated zeolite having a $SiO_2$ to $Al_2O_3$ molar ratio of 10-200 improves the performance/stability of the catalyst. Means and methods for quantifying the $SiO_2$ to $Al_2O_3$ molar ratio of a dealuminated zeolite are well known in the art and include, but are not limited to AAS (Atomic Absorption Spectrometer) or ICP (Inductively Coupled Plasma Spectrometry) analysis.

The zeolite is in the hydrogen form: i.e. having at least a portion of the original cations associated therewith replaced by hydrogen. Methods to convert an aluminosilicate zeolite to the hydrogen form are well known in the art. A first method involves direct ion exchange employing an acid. A second method involves base-exchange using ammonium salts followed by calcination.

Furthermore, the catalyst composition comprises a sufficient amount of hydrogenation metal to ensure that the catalyst has a relatively strong hydrogenation activity. Hydrogenation metals are well known in the art of petrochemical catalysts. Accordingly, it is preferred that the catalyst does not comprise secondary metals, such as tin, lead or bismuth, that inhibit the hydrogenation activity of the hydrogenation metal. Preferably, the hydrocracking/hydrodesulphurisation catalyst used in the process of the present invention accordingly comprises less than 0.01 parts tin and less than 0.02 parts lead and less than 0.01 parts bismuth (on the basis of 100 parts by weight of the total catalyst), preferably less than 0.005 parts tin and less than 0.01 parts lead and less than 0.005 parts bismuth (on the basis of 100 parts by weight of total catalyst). The catalyst composition preferably comprises 0.1-1 wt-% hydrogenation metal, more preferably 0.2-07 wt-% hydrogenation metal. In the context of the present invention, the term "wt %" when relating to the metal content as comprised in a catalyst composition relates to the wt % (or "wt-%") of said metal in relation to the weight of the total catalyst, including catalyst binders, fillers, diluents and the like. Preferably, the hydrogenation metal is at least one element selected from Group 10 of the periodic table of Elements. The preferred Group 10 element is platinum. Accordingly, the hydrocracking/hydrodesulphurisation catalyst used in the process of the present invention comprises a zeolite having a pore size of 5-8 Å, a silica ($SiO_2$) to alumina ($Al_2O_3$) molar ratio of 5-200 and 0.1-1 wt-% platinum (in relation to the total catalyst)

The hydrocracking/hydrodesulphurisation catalyst composition may further comprise a binder. Alumina ($Al_2O_3$) is a preferred binder. The catalyst composition of the present invention preferably comprises at least 10 wt-%, most preferably at least 20 wt-% binder and preferably comprises up to 40 wt-% binder. In one embodiment, the hydrogenation metal is deposited on the binder, which preferably is $Al_2O_3$.

In one embodiment, the hydrocracking/hydrodesulphurisation catalyst comprises a mixture of ZSM-5 and Pt-modified alumina ($Pt/Al_2O_3$) wherein the weight ratio of ZSM-5:$Pt/Al_2O_3$ is between 5:1 and 1:5, preferably between 3:1 and 1:3 and most preferably between 2:1 and 1:2. In the context of the present invention, it was surprisingly found that by selecting a hydrocracking/hydrodesulphurisation catalyst comprising a mixture of ZSM-5 and Pt-modified alumina, the BTX content of the hydrocracking product stream can be increased when compared to a hydrocracking/hydrodesulphurisation catalyst wherein platinum is deposited on the ZSM-5 zeolite.

The feedstream used in the process of the present invention is a mixture comprising C5-C12 hydrocarbons, preferably having a boiling point in the range of 30-195° C. Preferably, the feedstream mainly comprises C6-C8 hydrocarbons. Suitable feedstreams include, but are not limited to first stage hydro-treated pyrolysis gasoline, straight run naphtha, hydrocracked gasoline, light coker naphtha and coke oven light oil, FCC gasoline, reformate or mixtures thereof. The process of the present invention is particularly suitable for processing a hydrocarbon feedstream having a relatively high sulphur content, such as pyrolysis gasoline (pygas), straight run naphtha, light coker naphtha and coke oven light oil and mixtures thereof. Furthermore, it is preferred that the non-aromatic species comprised in the hydrocarbon feed are saturated (e.g. by prior hydrogenation) in order to reduce the exotherm within the catalyst bed used in the present process.

For instance, a typical composition of first stage hydro-treated pyrolysis gasoline may comprise 10-15 wt-% C5 olefins, 2-4 wt-% C5 paraffins and cycloparaffins, 3-6 wt-% C6 olefins, 1-3 wt-% C6 paraffins and naphthenes, 25-30 wt-% benzene, 15-20 wt-% toluene, 2-5 wt-% ethylbenzene, 3-6 wt-% xylenes, 1-3 wt-% trimethylbenzenes, 4-8 wt-% dicyclopentadiene, and 10-15 wt-% C9+ aromatics, alkylstyrenes and indenes; see e.g. Table E3.1 from Applied Heterogeneous Catalysis: Design, Manufacture, and Use of Solid Catalysts (1987) J. F. Le Page. However, also hydrocarbon mixtures that are depentanised and tailed so the concentrations of all the C6 to C9 hydrocarbon species are relatively high compared with the typical figures above can be advantageously used as a feedstream in the process of the present invention.

In one embodiment, the hydrocarbon feedstream used in the process of the present invention is treated so that it is enriched in mono-aromatic compounds. As used herein, the term "mono-aromatic compound" relates to a hydrocarbon compound having only one aromatic ring. Means and methods suitable to enrich the content of mono-aromatic compounds in a mixed hydrocarbon stream are well known in the art such as the Maxene process; see Bhirud (2002) Proceedings of the DGMK-conference 115-122.

The hydrocarbon feedstream used in the process of the present invention may comprise up to 300 wppm of sulphur (i.e. the weight of sulphur atoms, present in any compound, in relation to the total weight of the feed). It is an advantage of the process of the present invention that it is not necessary to subject the hydrocarbon feedstream to a desulphurisation treatment prior to subjecting said hydrocarbon feedstream to the hydrocracking treatment. Preferably, the feedstream comprises 10-300 wppm of sulphur wherein the hydrodealkylation product stream comprises 0.1-5 wppm of sulphur. Methods for the measurement of the sulphur content in a hydrocarbons stream are well-well known. Preferably, the sulphur content is measured using the IP 490 standard; see also ISO 20846:2011. Accordingly, samples are introduced into a pyrolysis furnace, where the sample is oxidised at high temperature in an oxygen atmosphere. All sulphur in the sample is oxidised to $SO_2$. The $SO_2$ is exposed to ultraviolet light, causing it to fluoresce. The light emitted by the fluorescence is detected by a photomultiplier, and the resulting signal is proportional to the sulphur content of the sample.

The hydrocracking/hydrodesulphurisation step is performed in the presence of an excess amount of hydrogen in the reaction mixture. This means that a more than stoichiometric amount of hydrogen is present in the reaction mixture that is subjected to hydrocracking. Preferably, the molar ratio of hydrogen to hydrocarbon species ($H_2$/HC molar ratio) in the reactor feed is between 1:1 and 4:1, preferably between 1:1 and 3:1 and most preferably between 1:1 and 2:1. In the context of the present invention, it was surprisingly found that a higher benzene purity in the product stream can be obtained by selecting a relatively low $H_2$/HC molar ratio. In this context the term "hydrocarbon species" means all hydrocarbon molecules present in the reactor feed such as benzene, toluene, hexane, cyclohexane etc. It is necessary to know the composition of the feed to then calculate the average molecular weight of this stream to be able to calculate the correct hydrogen feed rate. The excess amount of hydrogen in the reaction mixture suppresses the coke formation which is believed to lead to catalyst deactivation.

The hydrocracking product stream is subjected to separation by standard means and methods suitable for separating methane and unreacted hydrogen comprised in the hydrocracking product stream as a first separate stream, the LPG comprised in the hydrocracking product stream as a second separate stream and the BTX as a third separate stream. Preferably, the BTX is separated from the hydrocracking product stream by gas-liquid separation or distillation. One non-limiting example of such a separation method includes a series of distillation steps. The first distillation step, at moderate, temperature is to separate most of the aromatic species (liquid product) from the hydrogen, $H_2S$, methane and LPG species. The gaseous stream from this distillation is further cooled (to about −30° C.) and distilled again to separate the remaining aromatics species and most of the propane and butane. The gaseous product (mainly hydrogen, $H_2S$, methane and ethane) is then be further cooled (to about −100° C.) to separate the ethane and leave the hydrogen, $H_2S$ and methane in the gaseous stream that will be recycled to the reactor. To control the levels of $H_2S$ and methane in the reactor feed, a proportion of recycle gas stream is removed from the system as a purge. The quantity of material that is purged depends on the levels of methane and $H_2S$ in the recycle stream which in-turn depend on the feed composition. The purge stream will have the same composition as the recycle stream. As the purge will contain mainly hydrogen and methane it is suitable for use as a fuel gas or may be further treated (e.g. via a pressure swing adsorption unit) to separately recover a high purity hydrogen stream and a methane $H_2S$ stream which can be used as a fuel gas.

In a further embodiment, the present invention relates to a process for producing benzene from a feedstream comprising C5-C12 hydrocarbons, wherein the said process comprises the process for producing BTX of the present invention further comprising the step of contacting BTX (or only the toluene and xylenes fraction of said BTX produced)

with hydrogen under conditions suitable to produce a hydrodealkylation product stream comprising benzene and fuel gas.

It has been previously described that benzene of very high purity can be prepared by hydrodealkylation of a feedstream comprising aliphatic and aromatic hydrocarbons. Hydrodealkylation processes for the preparation of benzene are commercially used, for instance for converting the C6-C9 fraction of pyrolysis products obtained in steam crackers to benzene; see e.g. Handbook of Commercial Catalysts: Heterogeneous Catalysts ed. Howard F. Rase (2000) CRC Press p. 211-212 and Handbook of Petroleum Refining Processes ed. Robert A. Meyers (1986) Mcgraw-Hill p 2-3-2-7.

A major drawback of conventional hydrodealkylation processes is that a major fraction of the hydrocarbon feed is downgraded to fuel gas mainly consisting of methane. In the context of the present invention, it was surprisingly found that the amount of fuel gas (methane) produced by the method for producing benzene of the present invention can be significantly reduced by employing a multi-step process wherein first BTX is produced and subsequently the BTX (or the toluene and xylenes separated from said BTX) is subjected to hydrodealkylation.

The prior art discloses hydrodealkylation processes wherein the formation of methane is reduced. Such a process is described in WO 2008/015027 which provides a catalytic hydrodealkylation process using a catalyst consisting of a ZSM-5 catalyst having a Si/Al molar ratio of 5-100, platinum and molybdenum. In the hydrodealkylation process according to WO 2008/015027 A1 the process conditions are selected as such that the formation of methane is reduced. The relatively mild hydrodealkylation conditions that are needed to suppress methane formation have the disadvantage that the product stream is rich in toluene, which has a much lower market value than benzene.

WO 2010/102712 A2 describes a method for obtaining essentially pure benzene by hydrodealkylation wherein the non-aromatic hydrocarbons are removed from the stream that is fed to the hydrodealkylation reactor by extractive distillation. A disadvantage of this method is that a heterogeneous mixture of non-aromatic hydrocarbons is obtained that needs further separation and/or processing.

In the process for producing benzene, the separation step (b) may include a step wherein the benzene comprised in the hydrocracking product stream is separated from the toluene and xylenes before hydrodealkylation. The advantage of this separation step is that the capacity of the hydrodealkylation reactor is increased. The benzene can be separated from the intermediate aromatic stream by conventional distillation. By this method benzene can be easily separated from the other aromatic species. This method cannot be used to recover benzene from the feedstream of the process of the present invention comprising C5+ hydrocarbons as said feedstream contains several species with boiling points close to benzene. These species are almost completely reacted in the reactor section such that their concentrations in the hydrocracking product stream are sufficiently low to allow production of sufficiently pure benzene by distillation of the hydrodealkylation product stream.

Processes for hydrodealkylation of hydrocarbon mixtures comprising C6-C9 aromatic hydrocarbons are well known in the art and include thermal hydrodealkylation and catalytic hydrodealkylation; see e.g. WO 2010/102712 A2. Catalytic hydrodealkylation is preferred in the context of the present invention as this hydrodealkylation process generally has a higher selectivity towards benzene than thermal hydrodealkylation. Preferably catalytic hydrodealkylation is employed, wherein the hydrodealkylation catalyst is selected from the group consisting of supported chromium oxide catalyst, supported molybdenum oxide catalyst, platinum on silica or alumina and platinum oxide on silica or alumina.

The process conditions useful for hydrodealkylation, also described herein as "hydrodealkylation conditions", can be easily determined by the person skilled in the art. The process conditions used for thermal hydrodealkylation are for instance described in DE 1668719 A1 and include a temperature of 600-800° C., a pressure of 3-10 MPa gauge and a reaction time of 15-45 seconds. The process conditions used for the preferred catalytic hydrodealkylation are described in and preferably include a temperature of 500-650° C., a pressure of 3.5-7 MPa gauge and a Weight Hourly Space Velocity of 0.5-2 $h^{-1}$; see also Handbook of Commercial Catalysts: Heterogeneous Catalysts ed. Howard F. Rase (2000) Loc. cit.

The hydrodealkylation product stream is typically separated into a liquid stream (containing benzene and other aromatics species) and a gas stream (containing hydrogen, $H_2S$, methane and other low boiling point hydrocarbons) by a combination of cooling and distillation. The liquid stream may be further separated, by distillation, into a benzene stream, a C7 to C9 aromatics stream and a heavy aromatic stream. The C7 to C9 aromatic stream may be fed back to reactor section as a recycle to increase overall conversion and benzene yield. The heavy aromatic stream, which contains polyaromatic species such as biphenyl, is preferably not recycled to the reactor but may be exported as a separate product stream. The gas stream contains significant quantities of hydrogen may be recycled back, via a recycle gas compressor, to the reactor section. A recycle gas purge may be used to control the concentrations of methane and $H_2S$ in the reactor feed.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps. Mode(s) for Carrying Out the Invention.

The present invention will now be elucidated by the following non-limiting Examples.

Example 1 Preparation OF Hydrocracking/Hydrodesulphurisation Catalyst

A hydrocracking/hydrodesulphurisation catalyst has been prepared as follows.

Commercially available MFI type zeolite in the hydrogen form having a Si to Al molar ratio of about 100:1 was mixed with an alumina binder at a zeolite to binder weight ratio of about 9:1. The subsequent mixture was formed into spherical particles of approximately 1.6 mm diameter to provide bound zeolite particles.

Commercially available platinum-modified gamma-alumina particles (spheres of about 1.6 mm diameter) comprising 0.75 wt-% platinum were obtained. The platinum-modified gamma-alumina particles were having a total surface area of about 200 m²/g (measured by standard nitrogen BET method), a pore volume of approximately 0.7 cc/g and a mean pore diameter of approximately 20 nm.

Subsequently, the bound zeolite particles and the platinum-modified gamma-alumina articles were homogeneously mixed at a 1:1 weight ratio to provide the hydrocracking/hydrodesulphurisation catalyst composition.

Example 2 Hydrocracking/Hydrodesulphurisation of Pyrolysis Gasoline

Reaction tests were carried out using a 12 mm (inner diameter) stainless steel reactor tube containing a catalyst bed comprising 4 g of the hydrocracking/hydrodesulphurisation catalyst composition prepared in Example 1. At the start of the experiment the mixed catalyst bed was dried (to remove any adsorbed water) in situ in the test reactor at 140° C. under flowing hydrogen (100 ml/minute at 40 to 60 psig operating pressure) for a minimum of 2 hours. After this, the hydrogen flow and pressure were maintained whilst the reactor temperature was raised to the desired test temperature (typically ~500° C.) and held at this temperature for a minimum of 2 hours prior to the introduction of hydrocarbon feed. During these conditioning phases any Pt oxide present in the calcined catalyst is believed to be reduced to Pt metal. The reactor was operated at a temperature of 450-550° C., at a pressure of 100-400 psig (690-2760 kPa) and a weight hourly space velocity of 2-4 hr$^{-1}$. (WHSV is defined as hourly mass of hydrocarbon liquid fed to the reactor/mass of catalyst in the reactor).

During the tests the reactor product stream (hydrocracking product stream) was analysed via an online gas chromatograph fitted with a flame ionisation detector and calibrated to allow the identification and quantification of the hydrocarbon species. (Measured by using a Shimadzu GC-2014 fitted with a DB1 Column—60 m long; 0.32 mm internal diameter with 5.00 μm film thickness. Analysis test method conditions: —oven 50° C. hold 3 min, ramp 5° C. per min to 250° C. hold for 5 min. Helium carrier gas column flow 3.37 ml/minute; Total flow 107.4 ml/minute; Split ratio 30:1; Linear velocity 40.0 cm/second; Inlet pressure 25.8 psi.)

The hydrocracking product stream for the experiments carried out at each set of operating conditions are shown in table 2 as provided herein below.

Accordingly, it was found that a feedstream comprising a highly complex mixture of C5+ hydrocarbons can be converted into a hydrocracking product stream comprising LPG, an intermediate aromatic stream and less than 5 wt-% of methane by using the hydrocracking/hydrodesulphurisation process of the present invention.

TABLE 1

| Component | wt-% (By GC) |
|---|---|
| Total C6-C8 alkanes | 16.54 |
| C6 alkanes | 13.17 |
| C7 alkanes | 3.25 |

TABLE 1-continued

| Component | wt-% (By GC) |
|---|---|
| C8 alkanes | 0.12 |
| Total Aromatics | 75.36 |
| BTX | 74.85 |
| C9 + aromatics | 0.51 |
| Trimethyl Benzene | 0.03 |
| EMBzs | 0.21 |
| C10 + aromatics | 0.08 |
| Minors (unidentified) | 8.10 |

TABLE 2

| H₂:HC (molar ratio) | WHSV (hr⁻¹) | Pressure (kPa gauge) | Temp (° C.) | Benzene | Toluene | Total Aromatics | EB | CH₄ | Ethane | Propane | butanes | Total LPG | Pentane | hexane | MCP | 2-MP | 3-MP | Cyclohexane |
|---|---|---|---|---|---|---|---|---|---|---|---|---|---|---|---|---|---|---|
| 4 | 3 | 2760 | 450 | 43.7 | 20.3 | 73.47 | 3.7 | 0.5 | 3.4 | 12 | 5.6 | 21 | 0.37 | 0.2 | 0.3 | 0.36 | 0.31 | 0.49 |
|  |  | (400 psig) | 500 | 45.4 | 22.1 | 74.12 | 1.6 | 1.6 | 6.7 | 12.4 | 3.6 | 22.7 | 0.1 | 0.0 | 0.1 | 0.04 | 0.03 | 0.19 |
|  |  |  | 525 | 47.3 | 23.1 | 76.74 | 1.3 | 2.1 | 7.5 | 10.4 | 2.2 | 20.1 | 0.05 | 0.0 | 0.046 | 0.02 | 0.01 | 0.00 |
|  |  |  | 550 | 46.9 | 23.7 | 76.48 | 0.9 | 3.8 | 7.8 | 10.5 | 0.8 | 19.1 | 0.01 | 0.0 | 0 | 0.00 | 0.00 | 0.01 |
| 4 | 3 | 2070 | 450 | 45.6 | 21 | 78.21 | 5 | 0.3 | 2.4 | 8.7 | 4.4 | 15.5 | 0.38 | 0.4 | 0.3 | 0.39 | 0.41 | 0.31 |
|  |  | (300 psig) | 500 | 47.6 | 22.3 | 77.88 | 2.1 | 0.9 | 5.2 | 10.2 | 3.6 | 19 | 0.15 | 0.0 | 0.1 | 0.09 | 0.08 | 0.07 |
|  |  |  | 525 | 48.2 | 23.1 | 77.92 | 1.3 | 1.6 | 6.6 | 10 | 2.6 | 19.2 | 0.06 | 0.0 | 0.1 | 0.02 | 0.02 | 0.00 |
|  |  |  | 550 | 47.9 | 24.1 | 78.46 | 1 | 2.6 | 8.5 | 8.5 | 1.4 | 18.4 | 0.02 | 0.0 | 0 | 0.00 | 0.00 | 0.00 |
| 4 | 3 | 1380 | 450 | 47.4 | 20.7 | 76.74 | 3 | 0.3 | 3 | 9.9 | 4.8 | 17.7 | 0.39 | 0.4 | 0.3 | 0.43 | 0.40 | 0.31 |
|  |  | (200 psig) | 500 | 49 | 21.5 | 77.1 | 1.6 | 0.8 | 5.3 | 10.8 | 3.5 | 19.6 | 0.16 | 0.1 | 0.1 | 0.10 | 0.11 | 0.10 |
|  |  |  | 525 | 48.8 | 22.7 | 77.88 | 1.1 | 1.2 | 6.8 | 10.1 | 2.6 | 19.5 | 0.08 | 0.01 | 0.077 | 0.04 | 0.04 | 0.01 |
|  |  |  | 550 | 49 | 23.2 | 77.84 | 0.7 | 2.1 | 8.4 | 9.2 | 1.7 | 19.3 | 0.02 | 0.007 | 0.03 | 0.01 | 0.01 | 0.00 |
| 4 | 3 | 690 | 450 | 47.1 | 20.3 | 78.3 | 4.4 | 0.2 | 2.3 | 7.7 | 3.2 | 13.2 | 0.36 | 1 | 0.6 | 0.48 | 0.52 | 0.67 |
|  |  | (100 psig) | 500 | 49.1 | 21.5 | 77.89 | 1.7 | 0.5 | 5.1 | 9.6 | 3.1 | 17.8 | 0.19 | 0.3 | 0.2 | 0.20 | 0.19 | 0.18 |
|  |  |  | 550 | 49.9 | 22.8 | 78.14 | 0.5 | 1.4 | 7.9 | 9.2 | 1.9 | 19 | 0.04 | 0 | 0 | 0.02 | 0.02 | 0.01 |
| 4 | 4 | 1380 | 500 | 47.7 | 21.1 | 78.17 | 2.7 | 0.6 | 4.3 | 9.5 | 3.5 | 17.3 | 0.21 | 0.0 | 0.2 | 0.20 | 0.20 | 0.21 |
|  | 2 | (200 psig) |  | 48.7 | 22.7 | 77.71 | 1.2 | 0.9 | 5.8 | 10.3 | 3.3 | 19.7 | 0.11 | 0.0 | 0.1 | 0.07 | 0.06 | 0.01 |

"Total Aromatics" includes ethylbenzene as well as xylenes, C9 aromatics and C10 aromatics detected in the reactor products. "EB" means ethylbenzene, "MCP" means methylcyclopentane, "2MP" means 2-methylpentane and "3-MP" means 3-methylpentane.

In each case the molar ratio of hydrogen to hydrocarbons in the reactor feed was maintained at a molar-ratio of about 4:1. The typical composition of the pyrolysis gasoline used for these tests is shown in Table 1 as provided herein below:

Example 3 Influence of H₂/Hydrocarbon Molar Ratio on Benzene Purity

Reaction tests were carried out using the same catalyst and the same experimental setup as described in Example 2. The hydrocracking/hydrodesulphurisation process was carried out at a temperature of 495° C., a pressure of about 1380 kPa gauge (200 psig) and a WHSV of 1 hr$^{-1}$ (based on the weight of liquid feed) throughout the experiment using a plant derived pyrolysis gasoline with a composition as shown in the Table 3 below.

TABLE 3

| Component | wt-% (By GC) |
|---|---|
| Total C6-C8 alkanes | 13.14 |
| C6 alkanes | 12.25 |
| C7 alkanes | 0.81 |
| C8 alkanes | 0.08 |
| Total Aromatics | 72.89 |
| BTX | 71.78 |
| C9 + aromatics | 0.98 |
| Trimethyl Benzene | 0.07 |
| EMBzs | 0.48 |
| C10 + aromatics | 0.13 |
| Minors (unidentified) | 13.97 |

Accordingly, it was found that a higher benzene purity in the product stream can be obtained by selecting a relatively low $H_2$/HC molar ratio; see Table 4.

TABLE 4

| $H_2$:HC molar ratio | 2-MP | 3-MP | Hexane | MCP | Cyclo hexane | Total co-boilers | benzene | Benzene purity (wt-%) |
|---|---|---|---|---|---|---|---|---|
| 4:1 | 0.006 | 0.004 | 0.004 | 0.038 | 0.024 | 0.076 | 42.26 | 99.82 |
| 3:1 | 0.004 | 0.002 | 0.002 | 0.019 | 0.01 | 0.037 | 41.77 | 99.91 |
| 2:1 | 0.002 | 0.001 | 0.001 | 0.006 | 0.003 | 0.022 | 40.03 | 99.94 |
| 1.5:1 | 0.002 | 0.001 | 0.001 | 0.002 | 0.001 | 0.007 | 38.28 | 99.98 |

The invention claimed is:

1. Process for producing BTX comprising:
    (a) contacting a feedstream comprising C5-C12 hydrocarbons in the presence of hydrogen with a hydrocracking/hydrodesulphurisation catalyst comprising 0.1-1 wt-% hydrogenation metal in relation to the total catalyst weight and a zeolite having a pore size of 5-8 Å and a silica ($SiO_2$) to alumina ($Al_2O_3$) molar ratio of 5-200 under process conditions comprising a temperature of 450-580° C., a pressure of 300-5000 kPa gauge and a Weight Hourly Space Velocity of 0.1-10 $h^{-1}$ to produce a hydrocracking product stream comprising BTX; and
    (b) separating the BTX from the hydrocracking product stream;
    wherein the hydrocracking/hydrodesulphurisation catalyst comprises less than 0.01 parts tin, less than 0.02 parts lead, and less than 0.01 parts bismuth (on the basis of 100 parts by weight of total catalyst); and
    wherein the feedstream comprises benzene.

2. The process according to claim 1, wherein the hydrocracking product stream further comprises less than 5 wt-% of methane.

3. The process according to claim 1, wherein the hydrocracking product stream further comprises less than 1 wt-% of non-aromatic C6+ hydrocarbons.

4. The process according to claim 1, wherein the hydrocracking/hydrodesulphurisation conditions include a temperature of 470-550° C., a pressure of 600-3000 kPa gauge and a Weight Hourly Space Velocity of 0.2-6 $h^{-1}$.

5. The process according to claim 1, wherein the hydrogenation metal comprises an element selected from Group 10 of the periodic table of Elements.

6. The process according to claim 1, wherein the hydrogenation metal is platinum.

7. The process according to claim 1, wherein the hydrocracking/hydrodesulphurisation catalyst comprises a mixture of ZSM-5 and Pt-modified alumina (Pt/$Al_2O_3$) wherein the weight ratio of ZSM-5:Pt/$Al_2O_3$ is between 5:1 and 1:5.

8. The process according to claim 1 wherein the feedstream further comprises 10-300 wppm of sulphur and the hydrocracking product stream comprises less than 5 wppm of sulphur.

9. The process according to claim 1, wherein the molar ratio of hydrogen to hydrocarbon species ($H_2$/HC molar ratio) in the reactor feed is between 1:1 and 4:1.

10. The process according to claim 1, wherein the feedstream comprises pyrolysis gasoline, straight run naphtha, light coker naphtha and coke oven light oil or mixtures thereof.

11. The process according to claim 1, wherein the BTX is separated from the hydrocracking product stream by gas-liquid separation or distillation.

12. The process according to claim 1, further comprising performing hydrodealkylation by contacting said BTX with hydrogen to produce a hydrodealkylation product stream comprising benzene and fuel gas.

13. The process according to claim 12, wherein the hydrodealkylation is performed in the absence of a hydrodealkylation catalyst under hydrodealkylation conditions including a temperature of 600-800° C., a pressure of 3-10 MPa gauge and a reaction time of 15-45 seconds; or wherein the hydrodealkylation is performed in the presence of a hydrodealkylation catalyst selected from the group consisting of supported chromium oxide catalyst, supported molybdenum oxide catalyst, platinum on silica or alumina and platinum oxide on silica or alumina under hydrodealkylation conditions including a temperature of 500-650° C., a pressure of 3.5-7 MPa gauge and a Weight Hourly Space Velocity of 0.5-2 $h^{-1}$.

14. The process according to claim 2, wherein the hydrocracking product stream comprises less than 4 wt-% methane.

15. The process according to claim 4, wherein the hydrocracking/hydrodesulphurisation conditions include a temperature of 470-550° C., a pressure of 1000-2000 kPa gauge and a Weight Hourly Space Velocity of 0.4-2 $h^{-1}$.

16. The process according to claim 7, wherein the hydrocracking/hydrodesulphurisation catalyst comprises a mixture of ZSM-5 and Pt-modified alumina (Pt/$Al_2O_3$) wherein the weight ratio of ZSM-5:Pt/$Al_2O_3$ is between 3:1 and 1:3.

17. The process according to claim 1, wherein the separating of the BTX from the hydrocracking product stream is performed without solvent extraction.

18. Process for producing BTX comprising:
    (a) contacting a feedstream comprising C5-C12 hydrocarbons in the presence of hydrogen with a hydrocracking/hydrodesulphurisation catalyst comprising greater than 0.5 to 1 wt-% hydrogenation metal in relation to the total catalyst weight and a zeolite having a pore size of 5-8 Å and a silica ($SiO_2$) to alumina ($Al_2O_3$) molar ratio of 5-200 under process conditions comprising a temperature of 450-580° C., a pressure of 300-5000 kPa gauge and a Weight Hourly Space Velocity of 0.1-10 $h^{-1}$ to produce a hydrocracking product stream comprising BTX; and
    (b) separating the BTX from the hydrocracking product stream;
    wherein the hydrocracking/hydrodesulphurisation catalyst comprises less than 0.01 parts tin, less than 0.02 parts lead, and less than 0.01 parts bismuth (on the basis of 100 parts by weight of total catalyst); and
    wherein the feedstream comprises benzene.

19. Process for producing BTX comprising:
    (a) contacting a feedstream comprising C5-C12 hydrocarbons in the presence of hydrogen with a hydrocracking/hydrodesulphurisation catalyst comprising 0.1-1 wt-% hydrogenation metal in relation to the total catalyst weight and a zeolite having a pore size of 5-8 Å and a silica ($SiO_2$) to alumina ($Al_2O_3$) molar ratio of 5-200 under process conditions comprising a temperature of 450-580° C., a pressure of 300-5000 kPa gauge and a Weight Hourly Space Velocity of 0.1-10 $h^{-1}$ to produce a hydrocracking product stream comprising BTX; and (b) separating the BTX from the hydrocracking product stream;

wherein the hydrocracking/hydrodesulphurisation catalyst comprises less than 0.005 parts tin, less than 0.01 parts lead, and less than 0.005 parts bismuth (on the basis of 100 parts by weight of total catalyst), and wherein the feedstream comprises benzene.

20. The process according to claim 19, wherein the hydrocracking/hydrodesulphurisation catalyst is free of tin, bismuth, and lead.

* * * * *